United States Patent
Calderwood

(10) Patent No.: US 11,337,664 B2
(45) Date of Patent: May 24, 2022

(54) BARRIER-CONTAINED RADIOLOGICAL SENSOR HOLDER

(71) Applicant: Mitchell C Calderwood, Santa Barbara, CA (US)

(72) Inventor: Mitchell C Calderwood, Santa Barbara, CA (US)

( * ) Notice: Subject to any disclaimer, the term of this patent is extended or adjusted under 35 U.S.C. 154(b) by 413 days.

(21) Appl. No.: 16/350,420

(22) Filed: Nov. 15, 2018

(65) Prior Publication Data

US 2020/0155093 A1   May 21, 2020

(51) Int. Cl.
| | |
|---|---|
| *A61B 6/14* | (2006.01) |
| *G03B 42/04* | (2021.01) |
| *A61B 1/24* | (2006.01) |
| *A61B 6/00* | (2006.01) |

(52) U.S. Cl.
CPC .............. *A61B 6/4423* (2013.01); *A61B 1/24* (2013.01); *A61B 6/145* (2013.01); *G03B 42/042* (2013.01)

(58) Field of Classification Search
CPC ......... A61B 6/4423; A61B 6/145; A61B 1/24; G03B 42/042
See application file for complete search history.

(56) References Cited

U.S. PATENT DOCUMENTS

| | | | | |
|---|---|---|---|---|
| 5,001,738 A | * | 3/1991 | Brooks ................ | G03B 42/042 378/168 |
| 6,520,676 B1 | * | 2/2003 | Schmitz ................ | G03B 42/06 378/168 |
| 2003/0152196 A1 | * | 8/2003 | Bratslavsky ......... | G03B 42/042 378/170 |
| 2005/0265522 A1 | * | 12/2005 | Manley ................. | A61B 6/145 378/169 |
| 2010/0044267 A1 | * | 2/2010 | Tolibas-Spurlock .......... | B65D 65/466 206/524.7 |
| 2010/0177875 A1 | * | 7/2010 | Steward, Jr ............ | A61B 6/145 378/170 |

(Continued)

OTHER PUBLICATIONS

Albright Technologies—Silicone Rubber Properties—accessed Jan. 9, 2021 at https://albrightsilicone.com/types-and-properties/ (Year: 2021).*

*Primary Examiner* — David P Porta
*Assistant Examiner* — Jeremy S Valentiner
(74) *Attorney, Agent, or Firm* — Gordon E. Gray, III; Gray Law Firm

(57) ABSTRACT

The present invention is an improved barrier-contained radiological sensor holder. In particular, the present invention is directed to radiological sensor holder contained in a barrier to reduce or prevent contamination. The radiological sensor holder preferably comprises a sensor holder at least partly contained within a barrier having a closed end and an open end. The barrier preferably comprises elastomer latex material and the sensor holder preferably comprises a polymer-based material with a treated surface or material characteristics amenable to anchorage of the elastomer. Alternatively, the holder is a wood pulp-based material with naturally coarse or irregular surface characteristics providing anchorage infusion of the elastomer. The sensor holder preferably has a sleeve with a base, first and second sides, and an opposing face and a bite wing integrally formed with the sleeve along a spine on the base. The sensor holder may alternately include an expansion slot along the opposing face.

1 Claim, 3 Drawing Sheets

(56) References Cited

U.S. PATENT DOCUMENTS

2011/0017619 A1* 1/2011 Motoyama ............... A61B 6/14
                                                            206/305
2018/0028132 A1* 2/2018 Brenner ............... G03B 42/042

* cited by examiner

BARRIER-CONTAINED RADIOLOGICAL SENSOR HOLDER

TECHNICAL FIELD

The present invention is an improved barrier-contained radiological sensor holder. In particular, the present invention is directed to radiological sensor holder contained in a barrier to reduce or prevent contamination.

BACKGROUND ART

Digital radiological sensors generally fall into two categories: CMOS (complementary metal oxide semiconductor) and CCD (charge-coupled device). Each utilizes scintillators to convert x-rays into visible light. The sensitivity of these sensor chips generally does not allow for heat or chemical sterilization. Dental practitioners are required by the U.S. Food and Drug Administration to maintain these small, very expensive digital radiological sensors in a clean and un-contaminated state for use between patients. Pathogens should not be allowed to cross contaminate patients during any radiological procedure.

Current systems for maintaining oral radiological sensors in an uncontaminated state require the dental practitioner to first insert the sensor into a barrier. Barriers are typically made from flexible polyethylene plastic, elastomeric latex or nitrile rubber. All of these materials provide generally sufficient barriers. However, it is often difficult and time consuming to insert a sensor into a barrier as barriers should be tight fitting to the sensor. A tightly fitted barrier reduces the incidence of artifacts in resultant radiological images and reduces the incidence of choking reactions from patients. Even a small amount of excess barrier material protruding from the distal end of the sensor can cause a choking reaction.

Typically, the second step for the practitioner prior to capturing a radiological image with the sensor is to place the barrier-covered sensor into a sensor holder/positioner so that the sensor can be placed at the proper angle and position in the patient's oral cavity to capture the preferred image. An example of a sensor holder/positioner is shown in U.S. Pat. No. 6,520,676. This patent is incorporated herein by reference in its entirety.

Sensors come in a variety of sizes and shapes and therefore, consequently, a variety of holders are available as well. However, sensors fitted with a barrier in different manufacturer's holders can present problems with slack space, too tight a fit, additional handling time. This can also result in movement of sensor during image capture, damage to the sensor and additional time for the practitioner inserting the sensor. Additionally, a third item is often applied to cushion the holder and sensor so it does not irritate soft tissue in a patient's oral cavity. Accordingly, a device is needed that aids a dental practitioner in maintaining oral radiological sensors (regardless of size) in an uncontaminated state from patient to patient while providing a sensor positioning means for image capture and doing so in a more time efficient and cost effective way than is currently available.

SUMMARY OF THE INVENTION

The present invention is an improved barrier-contained radiological sensor holder. In particular, the present invention is directed to radiological sensor holder contained in a barrier to reduce or prevent contamination. The radiological sensor holder preferably comprises a sensor holder at least partly contained within a barrier having a closed end and an open end. The barrier preferably comprises elastomer latex material and the sensor holder preferably comprises a polymer-based material with a treated surface or material characteristics amenable to anchorage of the elastomer. Alternatively, the holder is a wood pulp-based material with naturally coarse or irregular surface characteristics providing anchorage infusion of the elastomer. The sensor holder preferably has a sleeve with a base, first and second sides, and an opposing face and a bite wing integrally formed with the sleeve along a spine on the base. The sensor holder may alternately include an expansion slot along the opposing face.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved barrier-contained radiological sensor holder.

To insert a prior art sensor holder/positioner by hand into any given barrier is difficult and time consuming. Often, the positioner itself may not fit properly within a given barrier. This would likely render its positioning qualities useless and can compromise the cross contamination integrity of any given barrier with tiny holes or obvious damage to the thin barrier material itself from, e.g. forcing the holder to inside the barrier. Therefore, hand insertion is not practical or not recommended in a clinical setting.

Figure 1:
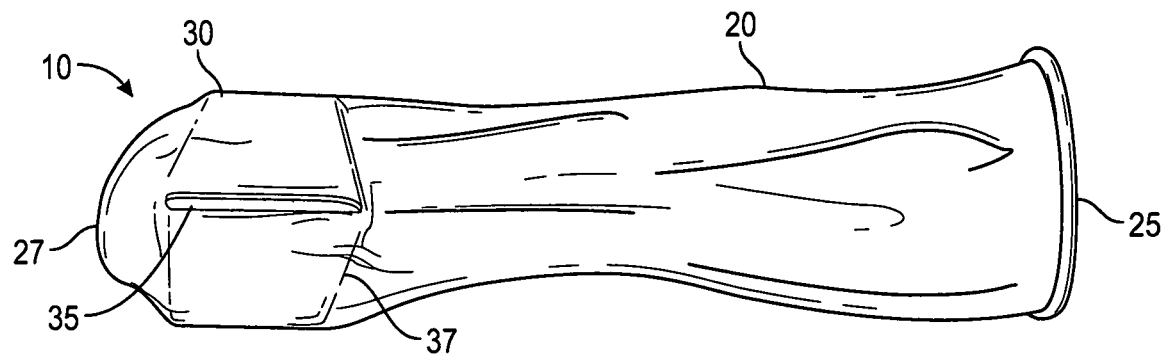
FIG. 1 is a top perspective view of a preferred embodiment of the invention.
Figure 3:
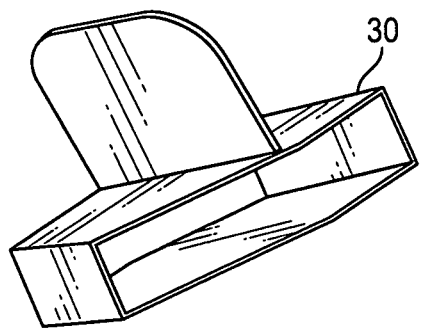
FIG. 3 is a side perspective view of a preferred embodiment of the sensor holder.

Referring now to FIG. 1, a top view of a preferred embodiment of the invention 10 is shown. A barrier sheath 20 is shown encapsulating a sensor holder 30. The barrier sheath 20 is preferably 0.1 mm to 4 mm in thickness. The sensor holder 30 preferably comprises a bitewing 35 and a sensor compartment 37. As shown, the sensor holder 30 is located inside the barrier sheath 20 as opposed to prior art devices where sensor holders/positioners are located external to the barrier. Referring now to FIG. 3, a preferred embodiment sensor holder 30, such as one described in U.S. Pat. No. 6,520,676, is shown without a barrier sheath 20. Preferably, a sensor holder is 1"×1.25" in size.

The combination of sensor holder 30 and barrier sheath 20 can be produced to be disposable (single use) or sterilizable (multiple use). A sterilizable version is preferably produced from materials that could withstand repeated sterilization cycles at temperatures up to 190° C. such as acrylonitrile butadiene styrene (ABS), nylon (polyamide heat stabilized) or polypropylene.

Preferably, to assemble the present invention 10, a sensor holder 30 is manufactured first then a barrier sheath 20 is applied using one of three preferred methods: 1) dipping; 2) molding; or, 3) spraying.

Figure 6:
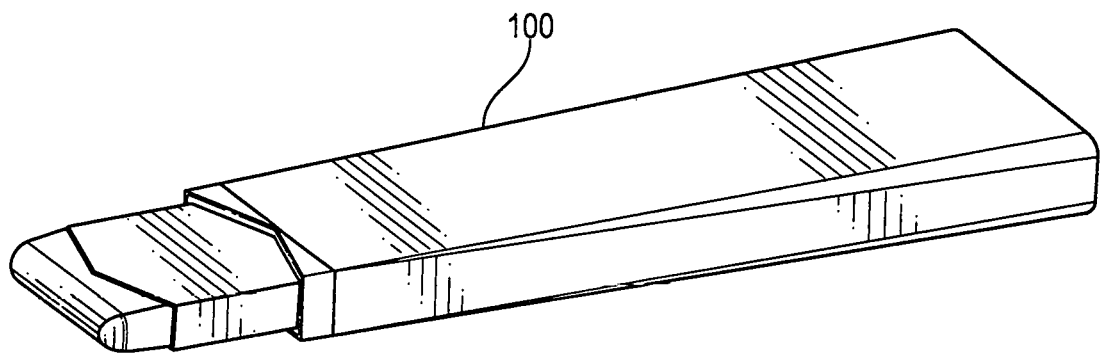
FIG. 6 is a side perspective view of preferred embodiment of a former alone.

Dipping Method:

A preferred method is "dipping" the sensor holder 30. Preferably, to encapsulate any given sensor holder 30 within an elastomer latex material such as, natural rubber latex or a synthetic elastomer such as nitrile, silicone, isoprene, etc., it will, in general, involve affixing the sensor holder 30 to a dipping former (a preferred embodiment of a former 100 is shown in FIG. 6) that would be dipped into the elastomer latex and subsequently dried or cured in an oven or UV cured and then harvested. The primary difficulty in producing a suitable finished product is adhesion of the elastomer to the surface of the holder 30. Preferably, the sensor holder 30 comprises a base material that promotes a low surface tension and has innate anchoring qualities such that the liquid elastomer will adhere to the holder and not flow off, "fish eye" or otherwise be repelled by the base material. A preferred material for the sensor holder 30 is plastic. This could be any number of polymers including, but not limited to, polyethylene, polypropylene, thermo-plastic urethanes, foamed styrenes, foamed urethanes, silicones and/or blends of various polymers. In the case of most plastics, however, adhesion and anchoring are more difficult than pulp-based materials described below. Polymers generally present very smooth surfaces and surface energies that do not promote the adhesion of elastomers. Accordingly, surface treatments for the sensor holder 30 are generally required when plastics are used. Preferred surface treatments include gamma ray treatment, electron beam treatment, flame treatment, chemical etching, or the use of various surface penetrates or coatings.

Alternative, yet also preferred, materials for the sensor holder are wood, bamboo or bagasse (sugar cane) pulp based materials. These materials while porous can be molded, die cut and conformed into suitable holder shapes with good anchoring and adhesion properties that could be over dipped.

Figure 4:
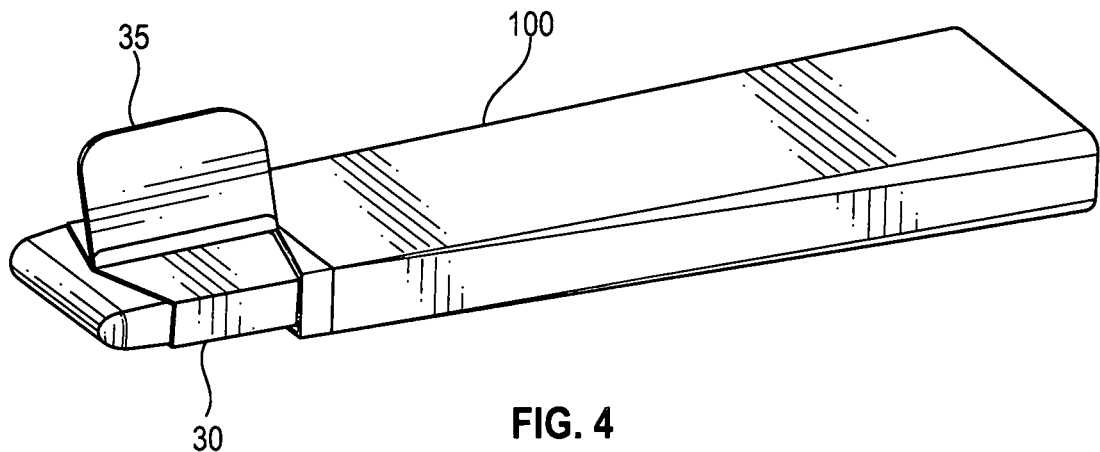
FIG. 4 is a side perspective view of a preferred embodiment of a sensor holder mounted on a former.
Figure 5:
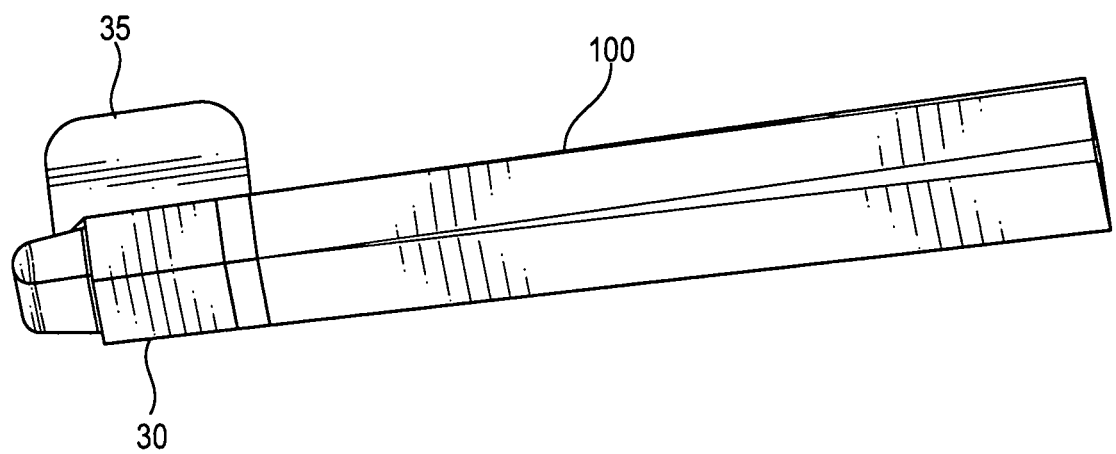
FIG. 5 is a side view of a preferred embodiment of a sensor holder mounted on a former.

Spraying Method:

The spraying method is another preferred method for encapsulating or partially encapsulating a sensor holder 30. Referring now to FIGS. 4-6, sensor holders 30 would be attached to formers 100 during the spraying method of encapsulation. FIGS. 4 and 5 show a preferred embodiment of a sensor holder 30 mounted on a preferred embodiment former 100. FIG. 6 shows a preferred embodiment former 100 alone. During a preferred spraying method, sensor holders 30 and formers 100 would preferably transit a spray booth during which an elastomer would be applied in coats over the sensor holders 30 and then cured. Curing is preferably by heat drying, gas, water, or chemical (catalyst) curing, or UV curing. A suitable adhesion and anchoring base material as described above for the sensor holder 30 would also be necessary for this method. If an area of the sensor holder 30, such as the bitewing 35, is not to be encapsulated by the barrier sheath 20, that portion of the sensor holder 30 can be covered to present elastomer from being sprayed thereon. Potentially, any elastomer can be used in the spraying method as long as the elastomer can be formulated into a spray-able viscosity. For example, an elastomer with a viscosity exceeding 3000 centipoise can become difficult to spray and there can be problems with running material, e.g. drips. On the other hand, dipping into a material of such a viscosity presents fewer drawbacks.

Plastic Film Encapsulation:

Sensor holders 30 could be encapsulated within various plastic films such as polyethylene, polypropylene, polyvinylidene chloride (Saran), elastic polymer films, etc. These films could be heat-sealed or heat shrunk around various holders. However, this is not a preferred method, as more prior work would be needed in cutting and assembling a patchwork of pieces together around the holder. In addition, this method would lend itself to small and microscopic holes that could compromise the barrier integrity against pathogens. Encapsulation can be accomplished by spraying, dipping, heat-shrinking or even painting.

Injection Molding:

The molding method is also a preferred method for encapsulating sensor holders 30 with barrier sheaths 20. Preferably, sensor holders 30 are inserted into a tooling mold (not shown). The tooling mold is preferably made specifically for plastic or film injection molding and over molded. This method could be done on a single cavity or multi cavity injection mold. The mold molds the barrier sheath 20 surrounding the sensor holder 30 and through heat and compression causes the barrier sheath material to weld to the holder's surface. The preferred elastomer for this method is liquid silicone rubber ("LSR"). A moving core in the mold is preferably used to prevent barrier material from filling unwanted areas. However, it should be noted that this method of production could have unfavorable processing drawbacks such as warped plastic holders from secondary, over mold temperatures that could create increased rates of rejected product. Also, there could be shrinkage problems between two differing materials. These could create increased rates of rejected product as well.

Barrier Coverage of the Sensor Holder:

The sensor holder 30 will, preferably, have one or two openings present to allow insertion of the sensor (not shown). Some prior art sensor holders have movable parts as well. The preferred barrier sheath 20 has a single opening 25 for insertion of the sensor (not shown). However, the sensor holder 30 as shown in FIG. 3 has two openings for insertion of the sensor. This allows a user to slide the sensor into the sensor holder 30 via the barrier opening 25 and center the sensor in the sensor holder 30 for proper location vis a vis the bitewing 35 of the sensor holder 30 for more precise image capture. Preferably, the bitewing 35 is positioned by the user between the teeth of a patient where the desired image is needed. The barrier sheath 20 is preferably formed around the sensor holder 30 opposite the barrier opening 25 such that a sensor has enough room to be centered in the sensor holder 30. Therefore, the barrier sheath 20 preferably extends beyond the sensor holder 30 forming a bubble 27 of protective barrier material encapsulating an end of the invention 10. The barrier sheath 20 preferably encapsulates the bitewing 35 as shown in FIG. 1.

Figure 2:
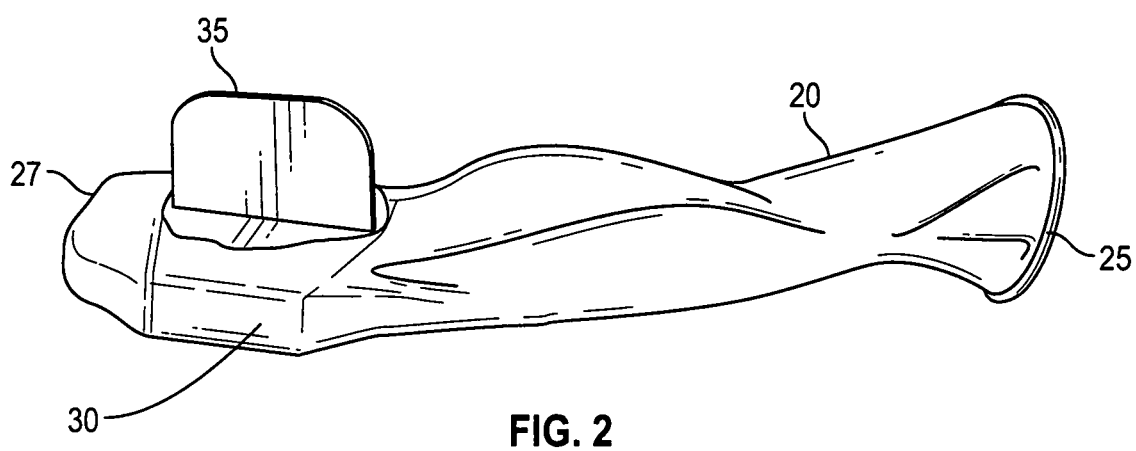
FIG. 2 is side perspective view of an alternative preferred embodiment of the invention.

Alternatively, the barrier sheath 20 can seal via adherence and surface anchoring to the sensor holder 30 such that the bitewing 35 or some portion thereof is exposed outside the barrier sheath 20 as shown in FIG. 2. Thus, the sensor would still be encapsulated within the barrier sheath 20 and sensor holder 30. This approach allows, for example, the bitewing 35 to be free of any barrier sheath material so that bite properties such as those disclosed in U.S. Pat. No. 6,520,676 can be seen and/or otherwise utilized.

The use of such an encapsulated sensor holder will allow for quicker and easier image capturing at a reduced cost in the clinical setting. Currently, using prior art devices, the practitioner must first apply a barrier to the sensor to prevent cross-contamination. Moreover, many patients also require the application of extra cushioning inside the barrier along the edges of the sensor as the edges can cause patient discomfort in soft tissue located in the roof of the mouth. Next, the sensor, enclosed within a barrier and likely padded as described, must be placed into a sensor holder in such a manner that it is secure and will not move during imaging. The practitioner then places the sensor and holder in a patient's oral cavity.

With the present invention, a practitioner preferably inserts the sensor through the barrier opening 25 of the barrier 20 into the sensor holder 30 and positions the sensor holder 30 in a patient's oral cavity. The barrier sheath 20 positioned on the outside of and surrounding the sensor holder 30 provides additional cushioning for soft tissue as well as providing the needed pathogen barrier. Moreover, the barrier sheath 20 contains the sensor holder 30 to provide stability for the sensor during imaging within a patient's oral cavity.

Figure 7:
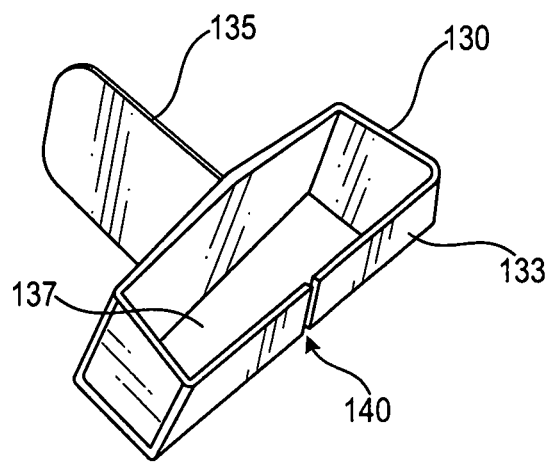
FIG. 7 is a top perspective view of an alternative embodiment of a sensor holder with an expansion slot; and, FIG. 8 is a top perspective view of an alternative embodiment of a sensor holder with an expansion slot in a barrier sheath.
Figure 8:
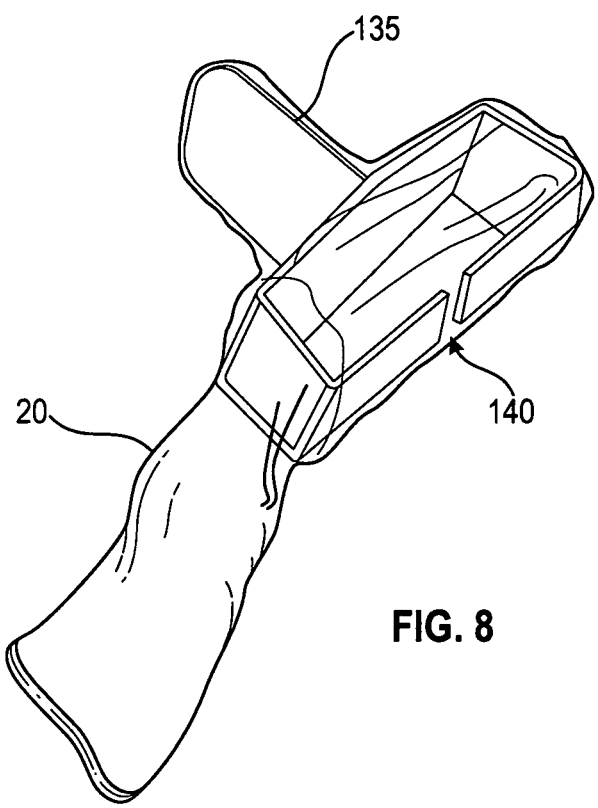

An alternative embodiment of the sensor holder described above can also be used in this invention. As shown in FIGS. 7 and 8, an alternative embodiment sensor holder 130 is shown. In particular, opposite of bitewing 135 is opposing face 133 surrounding sensor compartment 137. Opposing face 133 has an expansion slot 140 running along opposing face 133. The expansion slot 140 allows the sensor compartment 137 to expand to accept larger sensors. The elastomeric encapsulation of the barrier sheath 20, with sufficient durometer and elongation, will hold sensors of various sizes firmly in the barrier sheath 20 and sensor holder 130 under lateral expansion of the barrier sheath 20 to allow successful capture of clinical quality radiographic images. (Preferably, the material has an elongation between 400 and 1000% and durometer is from 20 Shore 00 to 30 Shore D.)

Thus, an improved barrier-contained radiological sensor holder is described above that aids a dental practitioner in maintaining oral radiological sensors (regardless of size) in an uncontaminated state from patient to patient while providing a sensor positioning means for image capture and doing so in a more time efficient and cost effective way than is currently available. In each of the above embodiments, the different positions and structures of the present invention are described separately in each of the embodiments. However, it is the full intention of the inventor of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or"

should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A radiological sensor holder comprising:
a sensor holder at least partly contained within a barrier sheath having a closed end and an open end where the sensor holder is between the open end and the closed end;
the barrier sheath comprises elastomer latex material and the sensor holder comprises a polymer-based material;
the sensor holder having a sleeve with a base, first and second sides, and an opposing face and a bitewing integrally formed with the sleeve along a spine on the base, where the bitewing is perpendicular to the sleeve;
where the barrier sheath comprises elastomer latex material welded to the sensor holder.

* * * * *